United States Patent [19]

Bushell et al.

[11] Patent Number: 4,689,337
[45] Date of Patent: Aug. 25, 1987

[54] INSECTICIDAL USE OF AZOLYL PROPANOLS

[75] Inventors: Michael J. Bushell; Paul A. Worthington, both of Berkshire, England

[73] Assignee: Imperial Chemical Industries PLC, London, England

[21] Appl. No.: 714,857

[22] Filed: Mar. 22, 1985

[30] Foreign Application Priority Data

Apr. 5, 1984 [GB] United Kingdom ............ 8408738
Apr. 6, 1984 [GB] United Kingdom ............ 8408952

[51] Int. Cl.$^4$ ............... A01N 43/653; A01N 43/647; C07D 249/08; C07D 249/04
[52] U.S. Cl. ...................... 514/383; 514/359; 514/399; 514/406; 548/255; 548/262; 548/341; 548/378
[58] Field of Search ............ 548/255, 262, 341, 378; 514/383, 399, 406, 359

[56] References Cited

U.S. PATENT DOCUMENTS 4,358,458 11/1982 Scharwachter et al. ......... 548/341
4,414,210 11/1983 Miller et al. ................... 514/383

FOREIGN PATENT DOCUMENTS 48548    3/1982  European Pat. Off. ........... 548/262
0055997  7/1982  European Pat. Off. ........... 548/262
0082340  6/1983  European Pat. Off. ........... 548/341
1532156 10/1978  United Kingdom .............. 548/262
1529818 11/1978  United Kingdom .............. 548/341
2110684  6/1983  United Kingdom .............. 548/262

Primary Examiner—Henry R. Jiles
Assistant Examiner—Kurt G. Briscoe
Attorney, Agent, or Firm—Cushman, Darby & Cushman

[57] ABSTRACT

Insecticidal and fungicidal compounds of the formula (I):

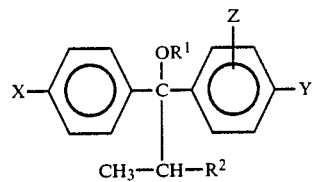

wherein $R^1$, X, Y, and Z are as defined in the specification and $R^2$ is a 1H-azol-1-yl group containing 2 or 3 nitrogen atoms are disclosed.

3 Claims, No Drawings

INSECTICIDAL USE OF AZOLYL PROPANOLS

This invention relates to novel azole derivatives having both fungicidal and insecticidal activities.

British Patent Specification No. 1,529,818 discloses a group of fungicidally useful triazole derivatives of formula:

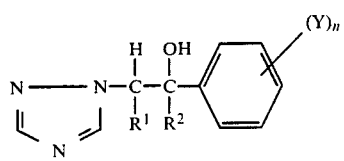

wherein each of $R^1$ and $R^2$, which may be the same or different, is hydrogen or optionally substituted hydrocarbyl; Y is hydrogen, halogen, nitro, alkyl, alkoxy or optionally substituted amino and n is an integer of 1 to 5. In the compounds specifically described in British Patent Specification No. 1,529,818 $R^1$ is hydrogen or optionally substituted benzyl and $R^2$ is hydrogen or methyl.

We have now discovered that within the broad group of compounds disclosed in British Patent Specification No. 1529818 there is a narrow group of previously undescribed compounds wherein $R^1$ is methyl and $R^2$ is halo-, haloalkyl-, or haloalkoxy- substituted phenyl which are not only effective fungicides but are also characterised in that they possess insecticidal properties unlike other similar compounds. These insecticidal properties may also be present in the corresponding compounds where triazole is replaced by imidazole or pyrazole.

Accordingly, the present invention provides compounds of formula:

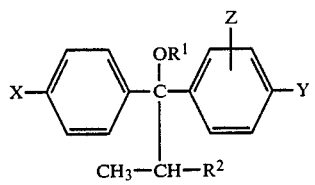

wherein X, Y and Z are each selected from halo, difluoromethyl, trifluoromethyl, difluoromethoxy and trifluoromethoxy and Z may also be hydrogen, $R^1$ is hydrogen alkyl of up to 6 carbon atoms or carboxylic acyl of up to 10 carbon atoms, and $R^2$ is a 1H-azol-1-yl group containing 2 or 3 nitrogen atoms.

Preferably Z and $R^1$ are both hydrogen, and X and Y are both the same and are selected from chloro, fluoro, trifluoromethyl and trifluoromethoxy. $R^2$ is preferably 1,2,4-1H-triazol-1-yl or 1H-pyrazol-1-yl. When $R^1$ is not hydrogen it is preferably a lower alkyl group such as methyl or ethyl or a lower carboxylic acyl group such as acetyl or trifluoroacetyl.

Particular compounds according to the invention are given in Table I wherein the meanings of X, Y, Z, $R^1$ and $R^2$ are set out for each compound. In the Table "Tr" indicates the 1,2,4-1H-triazol-1-yl group, "Py" indicates the 1H-pyrazol-1-yl group and "Im" indicates the 1H-imidazol-1-yl group.

TABLE I

| Compound No. | X | Y | Z | $R^1$ | $R^2$ |
|---|---|---|---|---|---|
| I | Cl | F | H | H | Tr |
| II | Cl | Cl | H | H | Tr |
| III | F | F | H | H | Tr |
| IV | F | F | Cl | 2-Cl | H | Tr |
| V | $CF_3$ | Cl | H | H | Tr |
| VI | Br | Cl | H | H | Tr |
| VII | Cl | Cl | 3-Cl | H | Tr |
| VIII | $CF_3$ | $CF_3$ | H | H | Tr |
| IX | Cl | $CF_3$ | H | H | Py |
| X | $CF_3$ | $CF_3$ | H | H | Py |
| XI | Cl | Cl | H | H | Py |
| XII | Br | Br | H | H | Py |
| XIII | I | I | H | H | Tr |
| XIV | $OCF_3$ | $OCF_3$ | H | H | Tr |
| XV | $CF_3$ | $CF_3$ | H | $CH_3$ | Tr |
| XVI | $CF_3$ | $CF_2$ | H | $C_2H_5$ | Tr |
| XVII | $CF_3$ | $CF_2$ | H | $COCH_3$ | Tr |
| XVIII | $CF_3$ | $CF_3$ | H | $COCF_3$ | Tr |
| XIX | $OCF_3$ | $OCF_3$ | H | H | Py |
| XX | Cl | Cl | H | H | Im |
| XXI | $CF_3$ | $CF_3$ | H | H | Im |
| XXII | $CHF_2$ | $CHF_2$ | H | H | Tr |
| XXIII | $OCHF_2$ | $OCHF_2$ | H | H | Tr |

Especially preferred compounds according to the invention include the following:

1,1-bis(4-trifluoromethylphenyl)-2-(1H-pyrazol-1-yl) propanol (Compound X), 1,1-bis(4-trifluoromethoxyphenyl)-2-(1H-pyrazol-1-yl) propanol (Compound XIX), 1,1-bis(4-trifluoromethylphenyl)-2-(1,2,4-1H-triazol-1-yl)-propanol (Compound VIII), and 1,1-bis(4-trifluoromethoxyphenyl)-2-(1,2,4-1H-triazol-1-yl)propanol (Compound XIV).

It will be appreciated that since the compounds of formula I contain at least one chiral centre (the carbon atom bearing the methyl group) and will contain two chiral centres when X is not the same as Y or when Z is not hydrogen, there exists the possibility of different isomeric and diastereoisomeric forms of the compounds. The invention includes within its scope all such isomers in isolation and mixtures thereof including racemic mixtures.

The compounds of formula I wherein $R^1$ is hydrogen may be prepared by a variety of processes such as those illustrated in outline in Scheme A.

Those compounds of formula I wherein $R^1$ and Z are both hydrogen and X and Y are the same may be prepared by the sequence of reactions represented by steps (k) and (m) of Scheme A. In step (k) a 2-halopropionic ester (II) is reacted with a 1H-azole of formula $R^2H$ to give a 2-(1H-azol-1-yl)propionic ester (III) which is further reacted in step (m) with two molar equivalents of a 4-X-phenylmagnesium halide (such as the bromide or chloride) under the conditions of the Grignard Reaction to yield the compound of formula I.

The compounds of formula I may also be prepared by the sequence of reactions represented by steps (a), (b) and (c) in Scheme A. In step (a) the 2-halopropionic ester (II) is reacted with one molar equivalents of a substituted phenyl magnesium halide of formula :

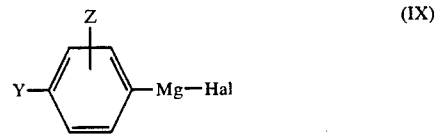

(wherein "hal" represents halogen, such as chlorine or bromine) to yield the α-halopropiophenone (IV) which is then reacted in step (b) with a 1H-azole of formula R²H to give a α-(1H-azol-1-yl)propiophenone (VII). This is converted into the compound of formula I by reaction in step (c) with a molar equivalent of the 4-X-phenylmagnesium halide. Alternatively, the similar procedure set out in Scheme A as steps (d), (e) and (f) may be used in which the 4-X-phenylmagnesium halide is reacted in step (d) with the 2-halopropionic ester to give the α-halopropiophenone (VI) which on reaction with the 1H-azole in step (e) is converted to the α-(1H-azol-yl)propiophenone (VIII). This latter compound is then reacted in step (b) with the substituted phenylmagnesium halide (IX) to give the compound of formula I.

In another process outlined in steps (g) and (j) in Scheme A the α-halopropiophenone (IV) is reacted with the 4-X-phenylmagnesium halide to give the oxirane (V), which is converted to the compound of formula I by reaction with a 1H-azole of formula R²H. The oxirane (V) may also be obtained by step (h) by reaction of a α-halopropiophenone (VI) with the substituted phenylmagnesium halide (IX).

The compounds of formula I wherein R¹ is hydrogen may be converted to the compounds of formula I wherein R¹ is alkyl by reaction with an appropriate alkyl halide in the presence of a base, and to compounds of formula I wherein R¹ is a carboxylic acyl group by reaction with an appropriate acyl halide of formula R¹CO-hal, such as the chloride, or an acid anhydride of formula (R¹CO)₂O.

Scheme A

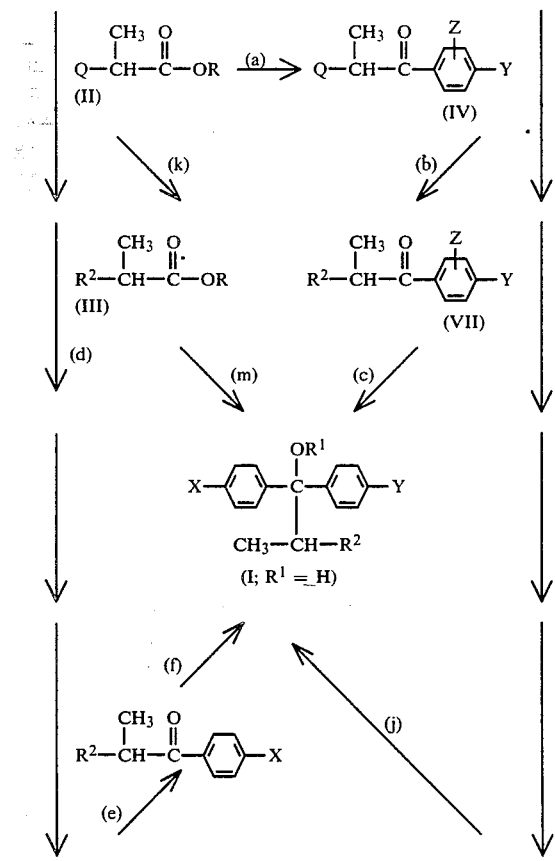

-continued
Scheme A

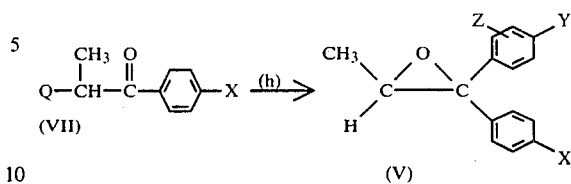

In Scheme A Q represents a suitable leaving group such as tosyloxy or halogen, preferably bromo or chloro, R is alkyl of up to 4 carbon atoms, and R², X, Y and Z have any of the meanings given hereinabove.

Many of the compounds of formula (III), (V), (VII) and (VIII) are believed to be novel and in a further aspect therefore the invention provides:

(i) A compound of formula:

wherein R² is a 1H-azol-1-yl group containing 2 or 3 nitrogen atoms, and R is an alkyl group of up to 4 carbon atoms;

(ii) A compound of formula:

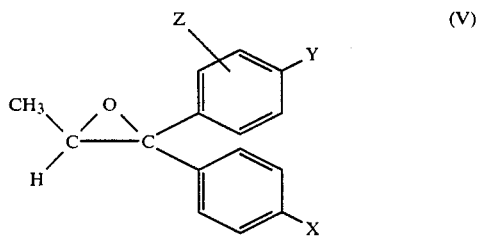

wherein X, Y and Z are each selected from halo, difluoromethyl, trifluoromethyl, difluoromethoxy and trifluoromethoxy and Z may also be hydrogen.

(iii) A compound of formula:

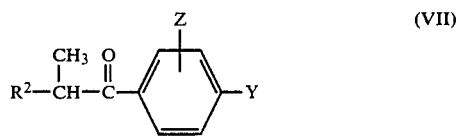

or formula

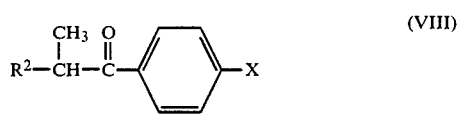

wherein X, Y and Z are each selected from halo, difluoromethyl, trifluoromethyl, difluoromethoxy and trifluoromethoxy and Z may also be hydrogen, and R² is a 1H-azol-1-yl group containing 2 or 3 nitrogen atoms.

In each of compounds III, VII and VIII R² is preferably 1H-pyrazol-1-yl or 1,2,4-1H-triazol-1-yl.

Specific compounds of formula III include
methyl 2-(1H-pyrazol-1-yl)propionate,
ethyl 2-(1H-pyrazol-1-yl)propionate, methyl 2-(1,2,4-1H-triazol-1-yl)propionate, and
ethyl 2-(1,2,4-1H-triazol-1-yl)propionate.

Specific compounds of formula V include
1,1-bis(4-fluorophenyl)-2-methyloxirane,
1,1-bis(4-chlorophenyl)-2-methyloxirane,
1,1-bis(4-trifluoromethylphenyl)-2-methyloxirane,
1,1-bis(4-trifluoromethoxyphenyl)-2-methyloxirane,
1,1-(4-chlorophenyl)-1-(4-trifluorophenylmethyl)-2-methyloxirane,
1-(4-chlorophenyl)-1-(4-fluorophenyl)-2-methyloxirane,
1-(2,4-dichlorophenyl)-1-(4-fluorophenyl)-2-methyloxirane, and
1-(4-chlorophenyl)-1-(3,4-dichlorophenyl)-2-methyloxirane.

Specific compounds of formula VII or formula VIII include
4-fluoro-α-(1H-pyrazol-1-yl)propiophenone,
4-chloro-α-(1H-pyrazol-1-yl)propiophenone,
4-trifluoromethyl-α-(1H-pyrazol-1-yl)propiophenone,
4-trifluoromethoxy-α-(1H-pyrazol-1-yl)propiophenone,
3,4-dichloro-α-(1,2,4-1H-triazol-1-yl)propiophenone,
2,4-dichloro-α-(1,2,4-1H-triazol-1-yl)propiophenone,
4-fluoro-α-(1,2,4-1H-triazol-1-yl)propiophenone,
4-trifluoromethyl-α-(1,2,4-1H-triazol-1-yl)propiophenone, and
4-trifluoromethoxy-α-(1,2,4-1H-triazol-1-yl)propiophenone.

The compounds of formula I may be used to combat and control infestations of insect pests and also other invertebrate pests, in particular, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the nonionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
*Aphis fabae* (aphids)
*Megoura viceae* (aphids)
*Musca domestica* (houseflies)
*Plutella xylostella* (diamond back month, larvae)
*Tetranychus cinnabarinus* (carmine spider mite)
*Tetranychus urticae* (red spider mites)
*Pahonychus ulmi* (citrus rust mite)
*Trialeuroides spp.* (white flies)
*Diabrotica spp.* (rootworms)
*Heliothis virescens* (tobacco budworm)
*Blatella germanica* (cockroaches)

EXAMPLE 1

This Example illustrates the preparation of 1,1-bis(4-chlorophenyl)-2-(1,2,4-1H-triazol-1-yl)propan-1-ol.

The Grignard reagent prepared from 4-chloroiodobenzene (0.03mol), magnesium turnings (0.03 g.atoms) and sodium dried ether (30 cm$^3$) was added dropwise to a stirred solution of α(1,2,4-1H-triazol-1-yl)-4-chloropropiophenone (0.015mol - Compound No 16, Table I, British Patent 1,153,706) dissolved in sodium dried tetrahydrofuran (30 cm$^3$) at such a rate so as to maintain gentle reflux. After the addition was complete the solution was heated at the reflux temperature for 3 hours, cooled to the ambient temperature and poured into a saturated solution of ammonium chloride. The ethereal solution was washed with water (3×50 ml.), and dried over anhydrous sodium sulphate. Removal of the solvent gave an oil which was purified by column chromatography (silica Merck 9385 eluted with ethyl acetate/petroleum ether 1:1) to give the required compound as a white crystalline solid up 164°–6°.

Analysis : $C_{17}H_{15}ClN_3O$ requires: C,58.6; H,4.3; N,121%. found: C,58.7; H,4.5; N, 11.8%.

EXAMPLE 2

Other compounds of Table I were prepared by analogous procedures to that set out in Example 1 but using the appropriate reactants, as follows:

1-(4-chlorophenyl)-1-(4-fluorophenyl)-2-(1,2,4-1H-triazol-1-yl)-propane-1-ol from α(1,2,4-1H-triazol-yl)-4-chloropropiophenone and 4-fluoroiodobenzene.

1-(2,4-Dichlorophenyl)-1-(4-fluorophenyl)-2-(1,2,4-1H-triazol-1-yl)propan-1-ol from α-(1,2,4-1H-triazol-1-yl)-4-fluoropropiophenone and 2,4-dichloroiodobenzene.

1,1-bis-(4-fluorophenyl)-2-(1,2,4-1H-triazol-1-yl)propan-1-ol (Compound No 8) from α-(1,2,4-1H-triazol-1-yl) and 4-fluoroiodobenzene.

EXAMPLE 3

This Example illustrates the preparation of 1,1-bis(4-trifluoromethylphenyl)-2-(1,2,4-1H-triazol-1-yl)-propan-1-ol.

(a) Preparation of α-chloro-4-trifluoromethylpropiophenone 4-trifluoromethylpropiophenone (26.3 g.) was dissolved in carbon tetrachloride (25 cm$^3$) and stirred at the ambient temperature. Sulphuryl chloride (19.3g 1.1 eq) in carbon tetrachloride (5 cm$^3$) was added. The mixture was heated to 90° C. for 4 hours then allowed to cool. The mixture was concentrated by evaporation of the solvent to give a colourless oil 30.5 g. (99%) This material was 93% pure by n.m.r., minor amounts of starting material and dichlorinated material being present.

Further purification by low temperature crystallisation was possible (the compound melts below room temperature).

N.m.r (CDCl$_3$)δ: 1.8(3H,d); 5.3(1H,q); 7.8 and 8.2(4H,ABq).

(b) Preparation of 2,2-bis(4-trifluoromethylphenyl)-3-methyloxirane n-Butyl-lithium (11.4 ml of a 6.3M solution in hexane, 0.018 mole) in tetrahydrofuran (THF) was added dropwise to a stirred solution of 4-iodotrifluoromethyl benzene (5 g., 0.018 mole) in dry THF (80 cm$^3$) under argon at −70° C. A small exotherm was observed, and after the addition was complete the mixture as stirred at −70° C. for 1 hour. α-Chloro-4- trifluoromethylpropiophenone (4.3 g., 0.018 mole) was dissolved in THF (5 cm$^3$) and added dropwise to the above solution. The mixture was stirred at −70° C. for 1.5 hours before warming slowly to ambient temperature. Water was added carefully, and the mixture was extracted with ether. The ether extracts were washed with water (3 times) then dried (MgSO$_4$) and concentrated by evaporation of the solvent under reduced pressure to give an oil. n-Butyl iodide present was removed by evaporation at a lower pressure to leave the oxirane as a residual oil.

$^1$H NMR (CDCl$_3$)δ: 1.2 (d,3H); 3.5 (q,1H); 7.5 (m,8H).

(c) Preparation of 1,1-bis(4-trifluoromethylphenyl)-2-(1,2,4-1H-triazol-1-yl)-propan-1-ol 1,2,4-1H-triazole was added to a stirred suspension of sodium hydride (0.86 g., 50% dispersion, washed with petroleum ether to remove oil) in dry dimethylformamide (40 cm$^3$). After stirring for 1.5 hours, the oxirane (formed in (b) above) dissolved in dimethylformamide (5 cm$^3$) was added slowly. The mixture was heated at 100° C. for 2 days, then cooled and poured into water, neutralised with dilute hydrochloric acid and the product extracted into ether, which was dried (MgSO$_1$) and concentrated by evaporation of the solvent.

The product was purified by preparative h.p.l.c. on silica, eluted with dichloromethane/ethylacetate 3:2, to give a white solid, m.p. 158°–160° C., yield 1.0 g.

Infra red: 3500cm$^{-1}$, O-H stretch.

N.M.R. (CDCl$_3$)δ: 1.51,(3H,dJ7H$_z$); 5.53,(1H,qJ7H$_z$); 5.77(1H,s); 7.4-7.8(8H,m); 7.85(1H,s); 8.12(1H,s).

Mass spectrum +ve C.I. MH$^+$ 416 (100%), 398(10%).

$C_{19}H_{15}F_6N_3O$ requires: C,54.95; H,3.61; N, 10.12%. Found: C,55.06; H,3.37; N,9.98%.

EXAMPLE 4

Other compounds of the invention were prepared according to the procedures of Example 3 from the appropriate reactants as follows:

1-(4-Chlorophenyl)-1-(4-trifluoromethylphenyl)-2-(1,2,4-1H-triazol-1-yl)-propan-1-ol, m.p. 164°–165° C.
$^1$H n.m.r (CDCl$_3$)δ: 1.52(d,3H); 5.53(q,1H); 5.76(s,1H); 7.4-7.75(m,8H); 7.93(s,1H); 8.16(s,1H).

1-(4-Bromophenyl)-1-(4-chlorophenyl)-2-(1,2,4-1H-triazol-1-yl)-propan-1-ol, m.p. 143°–144° C.
$^1$H n.m.r. (CDCl$_3$)δ: 1.53(d,3H); 5.38(q,1H); 5.50(s,1H); 7.2-7.65(m,8H); 7.82(s,1H); 8.01(s,1H).

Infra red (paraffin mull): 3250cm$^-$ (O-H stretch).
Mass spectrum: +ve C.I. 392,394(MH$^+$).

1-(4-Chlorophenyl)-1-(2,4-dichlorophenyl)-2-(1,2,4-1-H-triazol-1-yl)-propan-1-ol, m.p. 165°–168° C.
$^1$H n.m.r. (CDCl$_3$); 1.51(d,3H); 5.43(q,1H); 5.72(s,1H); 7.3-7.7(m,7H); 7.92(s,1H); 8.14(s,1H).

Infra red (paraffin mull) : 3160 cm$^-$ (O-H stretch).
Mass spectrum: +ve C.I. 382, 384, 386 (MH$^+$).

1,1-Bis-(4-Chlorophenyl)-2-(imidazol-1-yl)propan-1-ol by using imidazole in place of triazole.

EXAMPLE 5

This Example illustrates the preparation of 1,1-bis (4-trifluoromethylphenyl)-2-(1-1H-pyrazol-1-yl) propanol.

Pyrazole (0.6 g.) was added portion wise over 60 minutes to a stirred suspension of sodium hydride (obtained by washing 0.42 g. of a 50% dispersion in oil with petroleum ether (boiling range 40°–60° C.) to remove the oil) in dry dimethylformamide (30cm³) under an argon atmosphere at the ambient temperature and thereafter stirring the mixture for a further 90 minutes. 2,2-Bis(4-trifluoromethylphenyl)-3-methyloxirane (3.0 g.) was dissolved in the minimum quantity of dimethylformamide and the solution added dropwise to the stirred mixture. When the addition was complete the mixture was heated at the reflux temperature for 8 hours, and then kept at the ambient temperature for 16 hours. A little water was added and then the mixture was partitioned between water and diethyl ether, the ethereal phase separated, washed with water and dried over anhydrous magnesium sulphate and concentrated by evaporation of the ether under reduced pressure. The residual oil was subjected to preparative high performance liquid chromatography using a silica column eluted with a mixture of dichloromethane (5 parts by volume) and ethyl acetate (1 part by volume) to yield 1,1-bis(4-trifluoromethylphenyl)-2-(1-1H-pyrazol-1-yl) propanol (720 mg.) as a viscous oil, identified by infra red and n.m.r spectroscopy.

N.m.r (CDCl₃)δ: 1.5(d,3H); 3.8(broad s, 1H); 5.3(q, 1H) 6.1(m, 1H); 7.5(m,10H).

Infra red (liquid film): 3500 cm⁻¹.

EXAMPLE 6

By the use of procedures similar to those illustrated in Example 3a the following oxiranes may be prepared from the appropriate starting materials, as follows:
(a) 2,2-bis(4-chlorophenyl)-3-methyloxirane from 4-(2-chloro-1-oxopropyl)chlorobenzene and 4-iodochlorobenzene.
(b) 2-(4-chlorophenyl)-2-(4-trifluoromethylphenyl)-3-methyloxirane from 4-(2-chloro-1-oxopropyl) chloro benzene and 4-iodobenzotrifluoride.
(c) 2,2-bis(4-bromophenyl)-3-methyloxirane from 4-(2-chloro-1-oxopropyl)bromobenzene and 4-iodobromo benzene.
(d) 2,2-bis(4-trifluoromethylphenyl)-3-methyloxirane from 4-(2-chloro-1-oxopropyl)benzotrifluoride and 4-iodobenzotrifluoride.

EXAMPLE 7

By the use of procedures similar to those illustrated in Example 5 the following compounds were prepared from the appropriate oxiranes:
(a) 1,1-bis(4-chlorophenyl)-2-(1H-pyrazol-1-yl)propanol from 2,2-bis(4-chlorophenyl)-3-methyloxirane.

N.m.r (CDCl₃)δ: 1.45 (d,3H); 5.15(q,1H); 6.02(m,1H); 6.41 (broad s, 1H); 7.0–7.6(m,10H).
(b) 1-(4-chlorophenyl)-1-(4-trifluoromethylphenyl)-2-(1H-pyrazol-1-yl)propanol from 2-(4-chlorophenyl)-2-(4-trifluoromethylphenyl)-3-methyloxirane.

N.m.r (CDCl₃)δ: 1.5(d,3H); 5.2(q,1H); 6.1(m,1H); 7.4(m,11H).
(c) 1,1-bis(4-bromophenyl)-2-(1H-pyrazol-1-yl)propanol from 2,2-bis(4-bromophenyl)-3-methyloxirane.
(d) 1,1-bis(4-trifluoromethylphenyl)-2-(1H-pyrazol-1-yl) propanol from 2,2-bis(4-trifluoromethylphenyl)-3-methyloxirane.

EXAMPLE 8

This Example illustrates the preparation of 1,1-bis(4-trifluoromethoxyphenyl)-2-(1H-pyrazol-1-yl)propan-1-ol.

A solution of 4-trifluoromethoxybromobenzene (6.3 g.) in dry tetrahydrofuran (40 cm³) was added dropwise to a stirred mixture of magnesium turnings (0.62 g.), dry tetrahydrofuran (10 cm³) and a crystal of iodine under a nitrogen atmosphere. The reaction commenced after about 3 cm³ of the solution had been added and the mixture was warmed gently for a few minutes. When the addition was complete the mixture was stirred for 2 hours after which a solution of methyl 2-(1H-pyrazol-1-yl)propionate (2.0 g) in dry tetrahydrofuran (5.0 cm³) was added dropwise and the mixture then stirred for a further 2 hours at the ambient temperature. Finally the mixture was warmed to 40° C. to complete the reaction. The mixture was poured into water, acidified with dilute hydrochloric acid and extracted with two portions of diethyl ether 2×50 cm³. The extracts were combined, washed with water (3×50 cm³), dried over anhydrous magnesium sulphate and concentrated by removal of the solvent by evaporation under reduced pressure. The residual oil was subjected to purification by repeated chromatographic separation on a silica gel column eluted with a mixture of petroleum ether (boiling range 60°–80° C., 4 parts by volume) and ethyl acetate (1 part by volume) to yield 1,1-bis(4-trifluoromethoxyphenyl)-2-(1H-pyrazol-1-yl) propanol (500 mg.) as a pale yellow oil.

¹H NMR (CDCl₃)δ: 1.47 (d,3H); 5.20 (q,1H); 6.05 (t,1H); 6.56 (s,1H); 6.9–7.7 (m,10H)

EXAMPLE 9

This Example illustrates the preparation of 1,1-bis(4-trifluoromethoxyphenyl)-2-(1,2,4-1H-triazol-1-yl)-propanol.

A solution of 4-trifluoromethoxybromobenzene (9.3 g.) in dry tetrahydrofuran (40 cm³) was added dropwise to a stirred mixture of magnesium turnings (0.93 g.), dry tetrahydrofuran (15 cm³) and a crystal of iodine under a nitrogen atmosphere and at the ambient temperature. The reaction was observed to have commenced after 4 cm³ of the solution had been added. After the addition was complete the mixture was stirred for a further 2 hours. A solution of methyl 2-(1,2,4-1H-triazol-1-yl)propionate (3.0 g.) in dry tetrahydrofuran (5.0 cm³) was added dropwise to the mixture and after stirring for a further two hours at the ambient temperature the mixture was warmed to 40° C. for 3 hours. The mixture was then quenched with water, acidified with dilute hydrochloric acid and extracted with diethyl ether. The ethereal extract was washed with water (three times) and dried over anhydrous magnesium sulphate. The residual oil remaining after removal of the solvent by evaporation under reduced pressure was subjected to purification by hplc using a silica gel column eluted with a mixture of dichloromethane (3 parts by volume) and ethyl acetate (2 parts by volume) to give 1,1-bis(4-trifluoromethoxy-phenyl)-2-(1,2,4-1H-triazol-1-yl)propanol (1.0 g.) as a solid residue.

¹H NMR (CDCl₃)δ: 1.5 (d,3H); 5.38 (q,1H); 5.58 (s,1H); 6.9–7.7 (m,8H); 7.8 (s,1H); 8.0 (s,1H).

Infra red (paraffin mull): 3140 cm⁻¹.

EXAMPLE 10

This Example illustrates the preparation of a product consisting mainly of 1,1-bis(4-iodophenyl)-2-(1,2,4-1H-triazol-1-yl)propanol.

A solution of 1,4-diiodobenzene (8.5 g.) in dry tetrahydrofuran (40 cm$^3$) was added dropwise to a stirred mixture of magnesium turnings (0.62 g.), dry tetrahydrofuran (10 cm$^3$) and a crystal of iodine held in a flask in an ultrasonic bath which was warmed to initiate the reaction. The mixture was stirred for 2 hours after the addition had been completed. A solution of methyl 2-(1,2,4-1H-triazol-1-yl)propionate (2.0 g) in dry tetrahydrofuran (5.0 cm$^3$) was added to the mixture which was then kept at the ambient temperature for 16 hours. The product was isolated by the procedure given in the last previous example and then subjected to flash chromatography and to hplc to yield a product identified by mass spectroscopy and nmr spectroscopy as consisting of a mixture of 1,1-bis(4-iodo- phenyl)-2-(1,2,4-1H-triazol-1-yl)propan-1-ol (77%), 1-(4-iodophenyl)-1-phenyl-2-(1,2,4-1H-triazol-1-yl)- propan-1-ol (17%) and 1,1-diphenyl-2-(1,2,4-1H-triazol-1 yl)propan-1-ol (6%).

$^1$H NMR (CDCl$_3$)δ: [1.50 (d), 1.54 (d), 1.58 (d) - ratio 13:3:1], 5.3–5.55 (s,1H+q,1H); 7.1–8.5 (m).

Mass spectroscopy: MH$^+$, 280, 406, 532.

$^1$H NMR (CDCl$_3$)δ: 1.29 (d,6H); 1.58 (d,3H); 3.0 (m,1H); 5.62 (s,1H); 5.65 (q,1H); 7.3–7.8 (m,8H); 7.93 (s,1H); 8.18 (s,1H).

Infra red (liquid film): 3120 cm$^{-1}$.

EXAMPLE 11

This Example illustrates the preparation of 1,1-bis(4-trifluoromethylphenyl)-1-methoxy-2-(1,2,4-1H-triazolyl) propane.

1,1-Bis-(4-trifluoromethylphenyl)-2-(1,2,4-1H-triazolyl)propan-1-ol (0.5 g.) was added portionwise over a period of 15 minutes to a suspension of sodium hydride (58 mg, freed from dispersion in oil by washing with hexane) in dry dimethylformamide (50 cm$^3$) under a nitrogen atmosphere. The mixture was stirred for 2 hours then methyliodide (0.17 g.) in dimethylformamide (2 cm$^3$) was added dropwise. After stirring for 3 hours the mixture was partitioned between water and chloroform. The chloroform layer was separated, washed with water, dried over anhydrous magnesium sulphate and concentrated by evaporation of the solvent to yield 1,1-bis(4-trifluoro- methylphenyl)-1-methoxy-2-(1,2,4-1H-triazolyl)propane as a colourless oil.

NMR (CDCl$_3$)δ: 1.56 (d,3H); 2.95 (s,3H); 5.53 (q,1H); 7.2–7.7 (m,8H); 7.70, 7.80 (s,s,2H).

EXAMPLE 12

By the use of a similar procedure to that used in the previous example 1,1-bis(4-tetrafluoromethylphenyl)-1-ethoxy-2-(1,2,4-1H-tetrazolyl)propane was obtained as an oil from 1,1-bis(4-trifluoromethylphenyl)-2-(1,2,3-1H-triazol-1-yl)propanol and ethyliodide.

NMR (CDCl$_3$) δ: 1.16 (t,3H); 1.58 (d,3H); 3.0 (m,2H); 5.56 (q,1H); 7.2–7.7 (m,9H); 7.9 (s,1H).

EXAMPLE 13

This Example illustrates the preparation of 1,1-bis(4-trifluoromethylphenyl)-2-(1,2,4-1H-triazol-1-yl) propyl acetate.

1,1-Bis-(4-trifluoromethylphenyl)-2-(1,2,4-1H- triazol-1-yl)propan-1-ol (0.5 g.) was added carefully to a suspension of sodium hydride (60 mg., freed from dispersion in oil by washing with hexane) in dry dimethylformamide (20 cm$^3$) under a nitrogen atmosphere. After stirring the mixture for 2 hours acetyl chloride (0.1 g) was added and after a further 2 hours the mixture was diluted with water and extracted with chloroform. The chloroform layer was separated, washed with water, dried over anhydrous magnesium sulphate, and concentrated by evaporation of the solvent under reduced pressure to yield a residual oil which was purified by hplc and which solidified on trituration with petroleum ether (boiling range 60°–80° C.) to yield 1,1-bis(4-trifluoromethylphenyl)-2-(1,2,4-1H-triazol1-yl)propyl acetate (160 mg.).

NMR (CDCl$_3$) δ: 1.62 (d,3H); 2.03 (s,3H); 6.40 (q,1H); 7.0–7.8 (m,9H); 7.88 (s,1H).

Infra red (mull): 1750, 1335, 1240, 1140, 1076, 1023 cm$^{-1}$.

EXAMPLE 14

This Example illustrates the preparation of 1,1-bis(4-trifluoromethylphenyl)-2-(1,2,3-1H-triazol-1-yl)-propyl trifluoroacetate.

The procedure of the previous Example was followed except that trifluoroacetic anhydride (2 equivalents) was used in the place of acetyl chloride and mixture was heated for 90 minutes at 100° C. The product was obtained as an oil and purified by hplc.

$^1$H NMR (CDCl$_3$) δ: 1.23 (d,3H); 5.5 (q,1H); 7.1–7.75 (m,10H).

$^{19}$F-NMR (ppm): −63.32 (s); −63.48 (s); 84.87 (s).

p EXAMPLE 15

The insecticidal activity of compounds I to XIX and XXI is set out in the following Table as a grading of A, B or C where A indicates that 80–100% mortality was observed, B indicates that 50–79% mortality was observed and C indicates that 0–49% mortality was observed. The tests were conducted by supporting the test species on a medium (eg. leaves of a suitable food plant, or filter paper) and spraying the pests and medium (contact test—"CT" in the Table) or by spraying the medium before placing the pests thereon (residual test—"RT" in the Table). Assessment of mortality was made 72 hours after spraying except for houseflies (*Musca domestica*) where the assessment was made after 24 hours. In the test the compounds were used in the form of aqueous composition comprising 500 parts per million of the compound prepared by dissolving the compound in mixture of solvents consisting of 4 parts by volume by acetone and 1 part by volume of diacetone alchol and diluting the solution with water containing 0.01% by weight of a wetting agent ("Lissapol" NX - "Lissapol" is a Registered Trade Mark).

TABLE II

| CODE LETTERS (Table III) | TEST SPECIES | SUPPORT MEDIUM/FOOD | TYPE OF TEST | DURATION (days) |
| --- | --- | --- | --- | --- |
| PX | *Plutella xylostella* (Diamond back moth, larvae) | Cabbage leaf | CT | 6 |
| CP | *Chilo partellus* (maize stem bore) | Oil seed rape leaf | RT | 3 |

TABLE II-continued

| CODE LETTERS (Table III) | TEST SPECIES | SUPPORT MEDIUM/FOOD | TYPE OF TEST | DURATION (days) |
|---|---|---|---|---|
| HV | Heliothis viriscens (tobacco budworm) | Cotton leaf | RT | 3 |
| DB | Diabrotica balteata (rootworm larvae) | Filter paper/ maize seed | RT | 3 |
| BG | Blattella germanica (cockroach nymphs) | Plastic pot | RT | 3 |
| MD | Musca domestica (houseflies - adults) | Cotton wool/ sugar | CT | 1 |

TABLE III

| PRODUCT | MD | BG | HV | CP | PX | DB |
|---|---|---|---|---|---|---|
| I | C | — | C | — | A | C |
| II | C | — | A | — | A | C |
| III | C | — | A | — | C | C |
| IV | C | — | B | — | C | A |
| V | A | — | A | — | A | A |
| VI | C | — | A | — | A | C |
| VII | C | — | A | — | A | C |
| VIII | A | A | A | — | A | A |
| IX | A | C | C | — | C | B |
| X | A | A | A | — | A | A |
| XI | C | C | C | C | C | C |
| XII | A | C | C | — | — | A |
| XIII | B | C | C | A | — | C |
| XIV | A | A | A | — | — | A |
| XV | B | A | A | — | — | A |
| XVI | B | C | A | — | — | C |
| XVII | C | A | C | A | — | C |
| XVIII | C | C | C | A | — | A |
| XIX | A | A | A | A | — | A |
| XXI | C | — | C | — | B | B |

"-" in TABLE III indicates not tested

EXAMPLE 16

The compounds of the invention wherein R² is 1,2,4-1H-triazol-1-yl were tested against a variety of foliar fungal diseases of plants. The technique employed was as follows:

The plants were grown in John Innes Potting Compost (No 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on Botrytis cinerea, Plasmopara viticola and Venturia inaequalis. The sprays were applied to maximum retention and the root drenches to a final concentration equivalent to approximately 40 ppm ai/dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on Erysiphe graminis in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:

4 = no disease
3 = trace—5% of disease on untreated plants
2 = 6–25% of disease on untreated plants
1 = 26–59% of disease on untreated plants
0 = 60–100% of disease on untreated plants The results are shown in Table IV.

TABLE IV

| COMPOUND NUMBER | PUCCINIA RECONDITA (WHEAT) | ERYSIPHE GRAMINIS (BARLEY) | PLASMOPARA VITICOLA (VINE) | BOTRYTIS CINEREA (GRAPE) | CERCOSPORA ARACHIDICOLA (PEANUT) | VENTURIA INAEQUALIS (APPLE) |
|---|---|---|---|---|---|---|
| II | 4 | 4 | 2 | 0 | 3 | 4 |
| I | 4 | 4 | 3 | — | 4 | 4 |
| IV | 4 | 4 | 3 | — | 4 | 4 |
| III | 4 | 4 | 3 | — | 4 | 4 |
| VII | 0 | 2 | 2 | 0 | 0 | 0 |
| XX | 2 | 4 | 0 | 0 | 0 | 0 |

We claim:

1. A method of combating insect pests at a locus which comprises applying to the locus an insecticidally effective amount of a compound of formula:

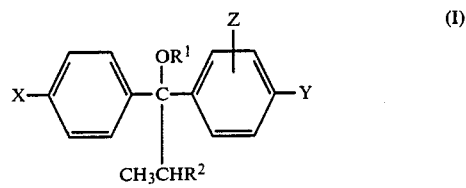

(I)

wherein X, Y and Z are each selected from halo, difluoromethyl, trifluoromethyl, difluoromethoxy and trifluoromethoxy and Z may also be hydrogen, R¹ is hydrogen, alkyl of up to 6 carbon atoms or carboxylic acyl of up to 10 carbon atoms, and R² is a 1H-azol-1-yl group of 2 or 3 nitrogen atoms as the sole hetero atoms.

2. A method according to claim 1 wherein the compound is one where X and Y are the same and are selected from chloro, fluoro, trifluoromethyl and trifluoromethoxy, Z and R¹ are both hydrogen and R² is 1,2,4-1H-triazol-1-yl or 1H-pyrazol-1-yl.

3. A compound according to claim 1 wherein the compound is selected from the group of compounds consisting of:

1,1-bis(4-trifluoromethylphenyl)-2-(1H-pyrazol-1-yl)propanol,
1,1-bis(4-trifluoromethoxyphenyl)-2-(1H-pyrazol-1-yl)propanol,
1,1-bis(4-trifluoromethylphenyl)-2-(1,2,4-1H-triazol-1-yl)triazol-1-yl)propanol, and
1,1-bis(4-trifluoromethoxyphenyl)-2-(1,2,4-1H-triazol-1-yl)propanol.

* * * * *